US005948821A

United States Patent [19]
Tatarintsev et al.

[11] Patent Number: 5,948,821
[45] Date of Patent: *Sep. 7, 1999

[54] METHODS OF USING AJOENE

[75] Inventors: Alexander V. Tatarintsev; Ali S. Turgiev, both of Moscow, Russian Federation; John B. Davidson, 2440 N. Lakeview Ave., Chicago, Ill. 60614

[73] Assignee: John B. Davidson, Chicago, Ill.

[*] Notice: This patent is subject to a terminal disclaimer.

[21] Appl. No.: 08/585,190

[22] Filed: Jan. 11, 1996

Related U.S. Application Data

[63] Continuation-in-part of application No. 08/445,146, May 19, 1995, which is a continuation-in-part of application No. 07/906,850, Jun. 30, 1992, abandoned.

[51] Int. Cl.$^6$ .................................................. A61K 31/105
[52] U.S. Cl. ........................... 514/707; 514/886; 514/887
[58] Field of Search ................................... 514/707, 886, 514/887

[56] References Cited

U.S. PATENT DOCUMENTS

| | | | |
|---|---|---|---|
| 4,126,676 | 11/1978 | Sanders | 424/98 |
| 4,341,762 | 7/1982 | Haast | 424/88 |
| 4,643,994 | 2/1987 | Block et al. | |
| 4,665,088 | 5/1987 | Apitz-Castro et al. | 514/420 |
| 4,876,281 | 10/1989 | Yoshida et al. | 514/517 |
| 5,066,658 | 11/1991 | Demers et al. | 514/707 |
| 5,093,122 | 3/1992 | Kodera | 424/195.1 |
| 5,380,646 | 1/1995 | Knight et al. | 424/1.69 |
| 5,464,855 | 11/1995 | Capiris et al. | 514/382 |

FOREIGN PATENT DOCUMENTS

| | | |
|---|---|---|
| 153881 | 9/1985 | European Pat. Off. . |
| 185324 | 6/1986 | European Pat. Off. . |
| WO 94/15953 | 7/1994 | WIPO .............................. C07K 5/00 |

OTHER PUBLICATIONS

Adler et al., "Sequential $^1$H NMR Assignments of Kistrin, a Potent Platelet Aggregation Inhibitor and Glycoprotein IIb–IIIa Antagonist", Biochemistry, vol. 31, pp. 1031–1039 (1992).

Adler et al., "Solution Structure of Kistrin, a Potent Platelet Aggregation Inhibitor and GP IIb–IIIa Antagonist," Science, vol. 253, pp. 445–448 (1991).

Adler et al., "Cysteine Pairing in the Glycoprotein IIbIIIa Antagonist Kistrin Using NMR, Chemical Analysis, and Structure Calculations," Biochemistry, vol. 32, pp. 282–289 (1993).

Au, et al., "A Common Precursor for a Putative Hemorrhagic Protein and Rhodostomin, a Platelet Aggregation Inhibitor of the Venom of *Calloselasma rhodostoma:* Molecular Cloning and Sequence Analysis," Biochemical and Biophysical Research Communications, vol. 181, No. 2, pp. 585–593 (1991).

Blobel, et al., "A potential fusion peptide and an integrin ligand domain in a protein active in sperm–egg fusion," Nature, vol. 356, pp. 248–252 (1992).

Calvete et al., "Identification of the Disulfide Bond Pattern in Albolabrin, and RGD–Containing Peptide from the Venom of *Trimeresurus albolabris:* Significance for the Expression of Platelet Aggregation Inhibitory Activity," Biochemistry, vol. 30, pp. 5225–5229 (1991).

Calvete, et al., "The Disulfide Bridge Pattern of Snake Venom Disintegrins, Flavoridin and Echistatin," FEBS Letters, vol. 309, No. 3, pp. 316–320 (1992).

Chang, et al., "Rhodostomin, An RGD–Containing Peptide Expressed From A Synthetic Gene In *Escherichia coli,* Facilitates The Attachment Of Human Hepatoma Cells," Biochemical and Biophysical Research Communications, vol. 190, No. 1 pp. 242–249 (1993).

Chao, et al., "Agkistrodon piscivorus piscivorus Platelet Aggregation Inhibitor: A Potent Inhibitor of Platelet Activation", Proc. Nat'l Acad. Sci. USA, vol. 86, pp. 8050–8054 (1989).

Chen, et al., "Proton NMR Assignments and Secondary Structure of the Snake Venom Protein Echistatin," Biochemistry, vol. 30, pp. 11625–11636 (1991).

Cooke et al., "Nuclear Magnetic Resonance Studies of the Snake Toxin Eschistatin $^1$H Resonance Assignments and Secondary Structure," Eur. J. Biochem, vol. 202, pp. 323–328 (1991).

Dalvit et al., "'$^1$H NMR Studies of Echistatin in Solution—Sequential Resonance Assignments and Secondary Structure," Eur. J. Biochem, vol. 202, pp. 315–321 (1991).

Dennis et al., "Platelet Glycoprotein IIb–IIIa Protein Antagonists from Snake Venoms: Evidence for a Family of Platelet–Aggregation Inhibitors," Proc. Nat'l Acad. Sci. USA, vol. 87, pp. 2471–2475 (1990).

Dennis et al., "Binding Interactions of Kistrin With Platelet Glycoprotein IIb–IIIa: Analysis by Site–Directed Mutagenesis," Proteins: Structure, Function and Genetics, vol. 15, pp. 312–321 (1993).

Fecondo, et al., "Synthtic Peptide Analogs of Intercellular Adhesion Molecule 1 (ICAM–1) Inhibit HIV–1 Replication in MT–2 Cells," Aids Research and Human Retroviruses, vol. 9, No. 8, pp. 733–740 (1993).

Gan, et al., "Echistatin, A Potent Platelet Aggregation Inhibitor From the Venom of the Viper, *Echis Carinatus*", The Journal of Biological Chemistry, vol. 263, No. 36, pp. 19827–19832 (1988).

Garsky et al., "Chemical Synthesis of Echistatin, a Potent Inhibitor of Platelet Aggregation from *Echis carinatus:* Synthesis and Biological Activity of Selected Analogs," Proc. Nat'l Acad. Sci. USA, vol. 86, pp. 4022–4026 (1989).

(List continued on next page.)

*Primary Examiner*—Keith D. MacMillan
*Attorney, Agent, or Firm*—Sheridan Ross P.C.

[57] ABSTRACT

The progression of infection and other pathologies produced by a viral infection may be inhibited by administering an effective dosage of Ajoene. Additionally, Ajoene has antitumor, anti-shock, and antiinflammation effects. In general, Ajoene may be used to treat any integrin-mediated disease or condition.

2 Claims, 1 Drawing Sheet

OTHER PUBLICATIONS

Glander, et al., "Beta 1-integrins of spermatozoa: a flow cytophotometric analysis," International Journal of Andrology, vol. 16, pp. 105–111 (1993).

Glaser, "Work on Cell-Adhesion-Based Interactions Beginning to Bear Fruit," Genetic Engineering News, vol. 15, No. 20, pp. 6–7 (1995).

Gould et al., "Disintegrins: A Family of Integrin Inhibitory Proteins from Viper Venoms $_{(43129B)}$"P.S.E.B.M., vol. 195, pp. 168–171 (1990).

Hardan, I., et al., Inhibition of Metastatic Cell Colonization in Murine Lungs and Tumor-Induced Morbidity by Nonpeptidic Arg-Gly-Asp Mimetics, 55 Int. J. Cancer 1023 (1993).

Hite, et al., "Sequence of a cDNA Clone Encoding the Zinc Metalloproteinase Hemorrhagic Toxin e from *Crotalus atrox:* Evidence for Signal, Zymogen, and Disintegrin-like Structures," Biochemistry, vol. 31, pp. 6203–6211 (1992).

Hite, et al., "cDNA Sequences for Four Snake Venom Metalloproteinases: Structure, Classification, and Their Relationship to Mammalian Reproductive Proteins," Archives of Biochemistry and Biophysics, vol. 308, No. 1, pp. 182–191 (1994).

Huang et al., "Mechanism of Action of the Antiplatelet Peptide, Arietin, From *Bitis Arietans* Venom," Biochimica et Biophysica Acta, vol. 1074 pp. 144–150 (1991).

Huang et al., "Purification and Characterization of an Antiplatelet Peptide, Arietin, from *Bitis Arietans* Venom", Biochimica et Biophysica Acta, vol. 1074, pp. 136–143 (1991).

Huang et al., "Triflavin, an Antiplatelet Arg-Gly-Asp-Containing Peptide, Is a Specific Antagonist of Platelet Membrane Glycoprotein IIb-IIIa Complex," J. Biochem, vol. 109, pp. 328–334 (1991).

Huang et al., "Halysin, an Antiplatelet Arg-Gly-Asp-Containing Snake Venom Peptide, As Fibrinogen Receptor Antagonist," Biochemical Pharmacology, vol. 42, No. 6, pp. 1209–1219 (1991).

Huang et al., "A Potent Antiplatelet Peptide, Triflavin, From *Trimeresurus Flavoviridis* Snake Venom," Biochem J., vol. 277, pp. 351–357 (1991).

Huang, et al., "Trigramin, A Low Molecular Weight Peptide Inhibiting Fibrinogen Interaction With Platelet Receptors Expressed on Glycoprotein IIb-IIIa Complex," The Journal of Biological Chemistry, vol. 262, No. 33, pp. 16157–16163 (1987).

Huang, et al., "Trigramin: Primary Structure and Its Inhibition of von Willebrand Factor Binding to Glycoprotein IIb/IIIa Complex on Human Platelets," Biochemistry, vol. 28, pp. 661–666 (1989).

Humphries, M.J., et al., Investigation of the Biological Effects of Anti-Cell Adhesive Synthetic Peptides that Inhibit Experimental Metastasis of B16-F10 Murine Melanoma Cells, 81 J. Clin. Invest. 782 (1988).

Kini et al., "Effects of Snake Venom Proteins on Blood Platelets," Toxicon, vol. 28, No. 12, pp. 1387–1422 (1990).

Kini et al., "Structural Domains in Venom Proteins: Evidence That Metalloproteinases and Nonenzymatic Platelet Aggregation Inhibitors (Disintegrins) From Snake Venoms are Derived by Proteolysis From A Common Precursor," Toxicon, vol. 30, No. 3, pp. 265–293 (1992).

Knudsen, et al., "Trigramin, an RGD-Containing Peptide from Snake Venom, Inhibits Cell-Substratum Adhesion of Human Melanoma Cells," Experimental Cell Research, vol. 179, pp. 42–49 (1988).

Mazur et al., "Ornatins: Potent Glycoprotein IIb-IIIa Antagonists and Platelet Aggreation Inhibitors From the Leech *Placobdella Ornata*," Eur. J. Biochem, vol. 202, pp. 1073–1082 (1991).

Musial, et al., "Inhibition of Platelet Adhesion to Surfaces of Extracorporeal Circuits by Disintegrins, RGD-Containing Peptides From Viper Venoms," Circulation, vol. 82, pp. 261–273 (1990).

Neeper et al., "Sequence of a cDNA Encoding the Platelet Aggregation Inhibitor Trigramin," Nucleic Acids Research, vol. 18, No. 14, p. 4255 (1990).

Omori-Satoh, et al., "Purification and Characterization of Cytotoxic Factors in the Venom of the *Okinawa Habu* (*Trimeresurus Flavoviridis*)," Toxicon, vol. 24, Nos. 11–12, pp. 1045–1053 (1986).

Paine et al., "Purification, Cloning, and Molecular Characterization of a High Molecular Weight Hemorrhagic Metalloprotease, Jararhagin, from *Bothrops Jararaca* Venom," The Journal of Biological Chemistry, vol. 267, No. 32, 22869–22876 (1992).

Perez, et al., "In Vivo Activity of Ajoene against Rodent Malaria," Antimicrobial Agents and Chemotherapy, vol. 38, pp. 337–339 (1994).

Rucinski et al., "Batroxostatin, an Arg-Gly-Asp-containing peptide from *Bothrops atrox*, is a potent inhibitor of platelet aggregate interaction with fibronectin," Biochimica et Biophysica Acta, vol. 1054, pp. 257–262 (1990).

Sato, et al., "Echistatin Is a Potent Inhibitor of Bone Resorption in Culture," Journal of Cell Biology, vol. 111, pp. 1713–1723 (1990).

Saudek et al., "Three-Dimensional Structure of Echistatin, the Smallest Active RGD Protein," Biochemistry, vol. 30, pp. 7369–7372 (1991).

Saudek et al., "The Secondary Structure of Echistatin from $^1$H-NMR, Circular-Dichroism and Raman Spectroscopy," Eur. J. Biochem, vol. 202, pp. 329–338 (1991).

Savage et al., "Binding of the Snake Venom-Derived Proteins Applaggin and Echistatin to the Arginine-Glycine-Aspartic Acid Recognition Site(s) on Platelet Glycoprotein IIb-IIIa Complex Inhibits Receptor Function," The Journal of Biological Chemistry, vol. 265, No. 20, pp. 11766–11772 (1990).

Scarborough et al., "Design of Potent and Specific Integrin Antagonists," The Journal of Biological Chemistry, vol. 268, No. 2, pp. 1066–1073 (1993).

Scarborough, et al., "Barbourin—A GPIIb-IIIa-Specific Integrin Antagonist From the Venom of *Sistrurus M. Barbouri*," The Journal of Biological Chemistry, vol. 266, No. 15, pp. 9359–9362 (1991).

Scarborough et al., "Characterization of the Integrin Specificities of Disintegrins Isolated from American Pit Viper Venoms," The Journal of Biological Chemistry, vol. 268, No. 2, pp. 1058–1065 (1993).

Seymour et al., "Decorsin—A Potent Glycoprotein IIb-IIIa Antagonist and Platelet Aggregation Inhibitor From the Leech *Macrobdella Decora*," The Journal of Biological Chemistry, vol. 265, No. 17, pp. 10143–10147 (1990).

Shebuski et al., "Characterization and Platelet Inhibitory Activity of Bitistatin, a Potent Arginine-Glycine-Aspartic Acid-containing Peptide from the Venom of the Viper *Bitis arietans*," The Journal of Biological Chemistry, vol. 264, No. 36, pp. 21550–21556 (1989).

Shebuski et al., "Acceleration of Recombinant Tissue–Type Plasminogen Activator–Induced Thrombolysis and Prevention of Reocclusion by the Combination of Heparin and the Arg–Gly–Asp–Containing Peptide Echistatin in a Canine Model of Coronary Thrombosis," Circulation, vol. 82, pp. 169–177 (1990).

Sheu et al., "Triflavin, an Arg–Gly–Asp–Containing Antiplatelet Peptide Inhibits Cell–Substratum Adhesion and Melanoma Cell–Induced Lung Colonization," Jpn. J. Cancer Res., vol. 83, pp. 885–893, Aug. (1992).

Soszka et al., "Inhibition of Murine Melanome Cell–Matrix Adhesion and Experimental Metastasis by Albolabrin, an RGD–containing Peptide Isolated from the Venom of *Trimeresurus albolabris*," Experimental Cell Research, vol. 196, pp. 6–12 (1991).

Takeya, et al., "The Complete Amino Acid Sequence of the High Moleuclar Mass Hemorrhagic Protien HR1B Isolated from the Venom of *Trimeresurus flavoviridis*," The Journal of Biological Chemistry, vol. 265, No. 27, pp. 16068–16073 (1990).

Takeya et al., "Coagulation Factor X Activating Enzyme from Russell's Viper Venom (RVV–X), A Novel Metalloproteinase With Disintegrin (Platelet Aggregation Inhibitor)—Like and C–Type Lectin–Like Domains," The Journal of Biological Chemistry, vol. 267, No. 20, pp. 14109–14117 (1992).

Takeya et al., "Primary Structures of Platelet Aggregation Inhibitors (Disintegrins) Autoproteolytically Released from Snake Venom Hemorrhagic Metalloproteinases and New Fluorogenic Peptide Substrates for These Enzymes," J. Biochem, vol. 113, pp. 473–483 (1993).

Weber, et al., "In Vitro Virucidal Effects of *Allium sativum* (Garlic) Extract and Compounds," Planta Med., vol. 58, pp. 417–423 (1992).

Williams, et al., "Elegantin and Albolabrin Purified Peptides From Viper Venoms; Homologies With the RGDS Domain of Fibrinogen and Von Willebrand Factor," Biochimica et Biophysica Acta, vol. 1039, pp. 81–89 (1990).

Yamakawa et al., "Primary Structures of Cytotoxic Factors Isolated from Habu (*Trimeresurus Flavoviridis*) Venom," J. Biochem., vol. 109, pp. 667–669 (1991).

Bone, "The Pathogenesis of Sepsis," Annals of Internal Medicine, vol. 115, pp. 457–469 (1991).

Broaddus et al., "Neutralizatioin of IL–8 Inhibits Neutrophil Influx In A Rabbit Model Of Endotoxin–Induced Pleruisy," Journal of Immunology, vol. 152, pp. 2960–2967 (1994).

Brodt et al., "Tumor Cell Adhesion To Frozen Lymph Node Sections—A Correlate Of Lymphatic Metastasis In Breast Carcinoma Models Of Human And Rat Origin," Breast Cancer Research and Treatment, vol. 17, pp. 109–120 (1990).

Feuerstein et al., "Prostaglandins, Leukotrienes, And Platelet–Activating Factor In Shock," Am. Rev. Pharmacol. Toxicol., vol. 27, pp. 301–313, 1987.

Fleckenstein et al., "Comparison of the Efficacy Of Mechanistically Different Antioxidants In The Rat Hemorrhagic Shock Model," Circulatory Shock, vol. 35, pp. 223–230 (1991).

Hub et al., "Mechanism Of Chemokine–Induced Leukocyte Adhesion And Emigration," ChemoattractantLigands And Their Receptors, Chapter 13, pp. 301–325, (1996).

Harlan et al., "In Vivo Models Of Leukocyte Adherence To Endothelium," Adhesion, Chapter 6, pp. 117–150 (1992).

Henderson, "The Role Of Leukotrienes In Inflammation," Ann. Intern. Med., vol. 121, pp. 684–697 (1994).

Hirvonen et al., "Anaphylactic Death: The Effect Of Aminoguanidine And Heparin On Histamine And Stress Hormones In Guinea Pigs," Z. Rechtsmed., vol. 102, pp. 297–304 (1989).

Hsueh et al., "Platelet–Activating Factor–Induced Ischemic Bowel Necrosis," AJP, vol. 122, No. 2, pp. 231–239 (1986).

Kellermann et al., "Phospholipase A in Acute Lung Injury After Trauma and Sepsis: Its Relation To The Inflammatory Mediators PMN–Elastase, C3a, and Neopterin," Klin Wochenschr vol. 67, pp. 190–195 (1989).

Kishimoto et al., "The Role Of Integrins In Inflammation," Inflammation: Basic Principles And Clinical Correlates, 2nd Ed., Chapter 20, pp. 353–406 (1992).

Lewis et al., "Leukotrienes And Other Products Of The 5–Lipoxygenase Pathway," Mechanisms Of Disease, vol. 323, No. 10, pp. 645–655 (1990).

Liu et al., "In Vitro Adhesion Assay," Adhesion, Appendix, pp. 189–193 (1992).

Liu et al., "Outlook For The Future," Adhesion, Chapter 8, pp. 183–187 (1992).

Mosby, "The Lung: Post–Traumatic Pulmonary Insufficiency," Multiple Organ Failure: Patient Care and Prevention (Chapter 10), pp. 235–263 (1990).

Mosby, Theories and Common Threads in Multiple Organ Failure, Multiple Organ Failure: Patient Care and Prevention (Chapter 26), pp. 473–486 (1990).

Mukaida, et al., "Novel Insight Into Molecular Mechanism Of Endotoxin Shock: Biochemical Analysis Of LPS Receptor Signaling In A Cell–Free System Targeting NF–κB And Regulation Of Cytokin Production/Action Through $\beta_2$ Integrin In Vivo," Journal Of Leukocyte Biology, vol. 59, pp. 145–151 (1996).

Ogata et al., "Protective Effects Of A Leukotriene Inhibitor And A Leukotriene Antagonist On Endotoxin–Induced Mortality In Carrageenan–Pretreated Mice," Infection And Immunity, vol. 60, No. 6, pp. 2432–2437 (1992).

Perbeck et al., "Prostaglandins $E_1$ And $E_2$ Antagonize Indomethacin–Induced Decrease In Survival Rate Of Haemorrhagically Shocked Rats," Acta Chir Scand, Suppl. vol. 500, pp. 91–94 (1980).

Samuelsson et al., "Leukotrienes and Lipoxins: Structures, Biosynthesis, And Biological Effects," Science, vol. 237, pp. 1171–1176, 1992.

Shenep et al., "Kinetics of Endotoxin Release During Antibiotic Therapy For Experimental Gram–Negative Bacterial Sepsis," The Journal Of Infectious Diseases, vol. 150, No. 3, pp. 380–388 (1984).

Simon et al., "Adult Respiratory Distress Syndrome," Inflammation: Basic Principles and Clinical Correlates, 2nd Ed., Chapt. 51, pp. 999–1016 (1992).

Spannagl et al., "A Purified Antithrombin III—Heparin Complex As A Potent Inhibitor Of Thrombin In Porcine Endotoxin Shock," Thrombosis Research, vol. 61, pp. 1–10 (1991).

Stevens et al., "Effects Of Anti–C5a Antibodies On The Adult Respiratory Distress Syndrome In Septic Primates," J. Clin Invest., vol. 77, pp. 1812–1816 (1986).

Svartholm et al., "Coagulation And Fibrinolytic Reactions In Experimental Porcine Septic Shock," Circulatory Shock, vol. 22, pp. 291–301 (1987).

Svartholm et al., "Pulmonary Vascular Response To Live *Escherichia Coli*," Circulatory Shock, vol. 22, pp. 173–183 (1987).

Terashita et al., "A Lethal Role Of Platelet Activating Factor In Anaphylactic Shock In Mice," The Journal Of Pharmacology And Experimental Therapeutics, vol. 243, No. 1, pp. 378–383 (1987).

Thörne et al., "Effect Of Ticlopidine And Prostaglandin E On Endotoxin–Induced Pulmonary Platelet Sequestration In Vivo," Circulatory Shock, vol. 20, pp. 61–69 (1986).

Tracey, "Tumor Necrosis Factor (Chachectin) In The Biology Of Septic Shock Syndrome," Circulatory Shock, vol. 35, pp. 123–128 (1991).

VanOtteren et al., "Compartmentalized Expression Of RANTES In a Murine Model Of Endotoxemia," The Journal Of Immunology, vol. 154, pp. 1900–1908 (1995).

Watanabe et al., "Prevention Of Endotoxin Shock By An Antibody Against Leukocyte Integrin $\beta_2$ Through Inhibiting Production And Action Of TNF," International Immunology, vol. 7, No. 7, pp. 1037–1046 (1995).

Yeston et al., "The Lung In Shock," Treatment Of Shock, Chapter 4, pp. 59–80.

Delaha et al., Chem. Abstracts, 102, 218177j, (1985).
Dausch et al., Chem. Abstracts, 113, 184048c, (1990).
Lichtenstein et al., Chem. Abstracts, 104, 45756h, (1986).
Meng et al., Chem. Abstracts, 115, 43950v, (1991).
Mohr, Chem. Abstracts, 108, 54653g, (1988).
Nakata et al., Chem. Abstracts, 79, 111680x (1973).
Perez et al., Chem. Abstracts, 120, 182454c, (1994).
Qian et al., Chem Abstracts, 106, 13095s, (1987).
Shah et al., Chem. Abstracts, 113, 204565z, (1990).
Soma et al., Chem. Abstracts, 116, 76349e, (1992).
Sumiyoshi et al., Chem. Abstracts, 113, 126061r, (1990).
Tadi et al., Chem. Abstracts, 116, 187586z, (1991).
Tsai et al., Chem. Abstracts, 104, 61572a, (1986).
Chemical Abstracts AN 1986:45756, Lichtenstein et al, EP 153881 A2, Mar. 1, 1985.
Chemical Abstracts AN 1990:91227, Belman et al., Jan. 1989.
Chemical Abstracts AN 1987:489878, Wagner et al., Jan. 1987.
WPIDS abstract AN 87–201984, Wajunaga Seiyaku KK, JP 62129224/, Jun. 11, 1987.
Chemical Abstracts AN 1987:400435, Saeed et al., Jan. 1985.

Bianchi et al., "Phenotypic And Functional Analysis Of Peripheral Blood Lymphocytes During Interferon–Alpha 2b Therapy In Multiple Myeloma Patients With Low Tumor Mass," Haematologica, vol. 76, pp. 383–388 (1991).

Bishop, "Molecular Themes In Oncogenesis," Cell, vol. 64, pp. 235–248 (1991).

Brodt, "Adhesion Mechanisms In Lymphatic Metastasis," Cancer and Metastasis Reviews, vol. 10, pp. 23–32 (1991).

Bukowski et al., "Phase I Trial Of Continuous Infusion Interleukin–2 and Doxorubicin In Patients With Refractory Malignancies," Journal of Immunotherapy, vol. 10, pp. 432–439 (1991).

Chambers et al., "Induction of Expression of Osteopontin (OPN; Secreted Phosphoprotein) in Metastatic, Ras–transformed NIH 3T3 Cells," Anticancer Research 12, pp. 43–48 (1992).

Chammas et al., "Integrins and Metastases: An Overview," Tumor Biol., vol. 12, pp. 309–320 (1991).

Dedhar, "Integrins and Tumor Invasion," BioEssays, vol. 12, No. 12, pp. 583–590 (1990).

Felding–Habermann et al., "Involvement Of Integrin αV Gene Expression in Human Melanoma Tumorigenicity," J. Clin. Invest., vol. 89, pp. 2018–2022 (1992).

Giancotti et al., "Integrin–Mediated Adhesion And Signaling In Tumorigenesis," Biochimica et Biophysica Acta, vol. 1198, pp. 47–64 (1994).

Heicappell et al., "Current Strategies For Immunotherapy Of Renal Cell Carcinoma," World Journal of Urology, vol. 9, pp. 204–209.

Horst et al., "Expression Of The Leucocyte Integrin LFA–1 (CD11a/CD18) And Its Ligand ICAM–1 (CD54) In Lymphoid Malignancies Is Related To Lineage Derivation And Stage Of Differentiation But Not To Tumor Grade," Leukemia, vol. 5, No. 10, pp. 848–853 (1991).

Hermann et al., "Interleukin–2 Dose, Blood Monocyte And CD25+ Lymphocyte Counts As Predictors Of Clinical Response To Interleukin–2 Therapy In Patients With Renal Cell Carcinoma," Cancer Immunology Immunotherapy, vol. 34, pp. 111–114 (1991).

Hsiao et al., "Plasticity Of Integrin Expression By Nerve–Derived Connective Tissue Cells," J. Clin Invest., vol. 87, pp. 811–820 (1991).

Ingber, "Extracellular Matrix As A Solid–State Regulator In Angio Genesis: Identification Of New Targets For Anti–Cancer Therapy," Seminars In Cancer Biology, vol. 3, pp. 57–63 (1992).

Inghirami et al., "Down–Regulation Of LFA–1 Adhesion Receptors By C–myc Oncogene In Suman B Lymphoblastoid Cells," Science, vol. 250 pp. 682–686.

Juliano et al., "Adhesion Molecules In Cancer: The Role Of Integrins," Current Opinion In Cell Biology vol. 5, pp. 812–818 (1993).

Kortlepel et al., "Human Acute Myeloid Leukaemia Cells Express Adhesion Proteins And Bind To Bone Marrow Fibroblast Monolayers And Extracellular Matrix Proteins," Leukemia, vol. 7, No. 8 pp. 1174–1179 (1993).

Kramer et al., "Laminin–Binding Integrin $\alpha_7\beta_1$: Functional Characterization And Expression In Normal And Malignant Melanocytes," Cell Regulation, vol. 2, pp. 805–817 (1991).

Krief et al., "Acquisition Of Tumorigenic Potential In The Human Myoepithelial HBL100 Cell Line Is Associated With Decreased Expression Of HLA Class I, Class II And Integrin β3 And Increased Expression Of c–myc," Int. J. Cancer, vol. 43, pp. 658–664 (1989).

Mortarini et al., "Role Of The $\alpha_5\beta_1$ Integrin Receptor In The Proliferative Response Of Quiescent Human Melanoma Cells to Fibronectin[1]," Cancer Research, vol. 52, pp. 4499–4506 (1992).

Mueller et al., "Pre–Clinical Therapy Of Human Melanoma With Morpholino–Doxorubicin Conjugated To A Monoclonal Antibody Directed Against An Integrin On Melanoma Cells," Antibody, Immunoconjugates, and Radiopharmaceuticals, vol. 4, No. 2, pp. 99–106 (1991).

Olive et al., "Cell Surface Expression Of ICAM–1 (CD54) And LFA–3 (CD58), Two Adhesion Molecules, Is Up–Regulated On Bone Marrow Leukemic Blasts After In Vivo Administration Of High–Dose Recombinant Interleukin–2," Journal Of Immunotherapy, vol. 10, pp. 412–417.

Pignatelli et al., "Low Expression of $\beta_1$, $\alpha_1$ and $\alpha_3$ Subunits Of VLA Integrins In Malignant Mammary Tumors," Journal Of Pathology, vol. 165, pp. 25–32 (1991).

Plantefaber et al., "Changes In Integrin Receptor On Oncogenically Transformed Cells," Cell, vol. 56, pp. 281–290 (1989).

Postigo et al., "Regulated Expression And Function Of CD11c/CD18 Integrin On Human B Lymphocytes. Relation Between Attachment To Fibrinogen And Triggering Of Proliferation Through CD11c/CD18," *J. Exp. Med.,* vol. 174, pp. 1313–1322 (1991).

Ramachandrula et al., "Tripeptide RGD–Dependent Adhesion Of Articular Chondrocytes To Synovila Fibroblasts," *Journal Of Cell Science,* vol. 101, pp. 859–871 (1992).

Ramos et al., "Role Of Laminin–Binding Integrin In The Invasion Of Basement Membrane Matrices By Fibrosarcoma Cells," *Invasion Metastasis,* vol. 11, pp. 125–138 (1991).

Schreiner et al., "Increased Tumorigenicity Of Fibronectin Receptor Deficient Chinese Hamster Ovary Cell Variants," *Cancer Research,* vol. 51, pp. 1738–1740 (1991).

Van Waes et al., "Overexpression Of Thge A9 Antigen/$\alpha 6\beta 4$ Integrin In Head And Neck Cancer," *Molecular Biology And Genetics,* vol. 25, No. 5, pp. 1117–1139.

Wake et al., "Calcium–Dependent Homotypic Adhesion Through Leukocyte Function–Associated Antigen–1/Intracellular Adhesion Molecule–1 Induces Interleukin–1 And Parathyroid Hormone–Related Protein Production On Adult T–Cell Leukemia Cells In Vitro," *Blood,* vol. 86, No. 6 pp. 2257–2267 (1995).

Witjes et al., "Characterizaion Of A Rat Oral Squamous Cell Carcinoma Cell Line UHG–RaC '93 Induced By 4–Nitroquinoline–1–Oxide In Vivo," *Carcinogenesis,* vol. 16, No. 11, pp. 2825–2832 (1995).

Zutter et al., "Decreased Expression Of Integrin Adhesive Protein Receptors In Adenocarcinoma Of The Breast," *American Journal Of Pathology,* vol. 137, No. 4, pp. 863–870 (1990).

G.F. Sud'ina, et al., *Biochimica et Biophysica Acta,* 1091, 257–60, Feb. 1991.

A.V. Tatarintsev, et al., International Conference On Molec. Biol. Aspects Of Diagnostics And Therapy Of AIDS, Conference poster and Abstract, Jul. 2–5, 1991.

A.V. Tatarintsev, et al., European Developmental Biology Congress, Conference abstract, Aug. 11–15, 1991.

A.V. Tatarintsev, et al., Keystone Symposia on Molec. & Cell. Biol., Conference abstract, Feb. 1992.

A.V. Tatarintsev, et al., Keystone Symposia on Molec. & Cell. Biol., Conference abstract, Mar. 1992.

E.V. Karamov, et al., Keystone Symposia on Molec. & Cell. Biol., Conference abstract, Apr. 4, 1992.

A.V. Tatarintsev, et al., Keystone Symposia on Molec. & Cell. Biol., Conference abstract, Apr. 4, 1992.

A. Tatarintsev, et al., VIII Int'l Conf. on AIDS, Conference abstract, Jul. 19–24, 1992.

R. Apitz–Castro, et al., *Thrombosis Research,* 32, No. 2, 155–69 (1938).

E. Block, et al., *J. Am. Chem. Soc.,* 106, No. 26, 8295–96 (1984).

E. Block, et al., *J. Am Chem. Soc.,* 108, No. 22, 7045–55 (1986).

R. Apitz–Castro, et al., *Thrombosis Research,* 42, 303–11 (1986).

R. Apitz–Castro, et al., *Biochemical and Biophysical Research Communications,* 141, No. 1, 145–50 (1986).

M.K. Jain, et al., *TIBS,* 12, No. 7, 252–54 (Jul. 1987).

M.P. Jamaluddin, et al., *Biochemical and Biophysical Research Communications,* 153, 1, 479–86 (1988).

R. Apitz–Castro, et al., *Drug Research,* 38(11), No. 7, 901–04 (1988).

J.C. Debouzy, et al., *European Biophysics Journal,* 17, 211–16 (1989).

F. Rendu, et al., *Biochemical Pharmacology,* 38, No. 8, 1321–28 (1989).

R. Apitz–Castro, et al., *Biochemica et Biophysica Acta,* 1094, No. 3, 269–80 (1991).

R. Apitz–Castro, et al., *Thrombosis and Haemotology,* 65, No. 6, No. 1380 at p. 1079 (1991) (abstract).

R. Apitz–Castro, et al., *Thrombosis and Haemotology,* 65, No. 6, No. 1603 at p. 1141 (1991) (abstract).

K.C. Srivestava, 4th Erfurt Conference on Platelets, June 22–27, 1992, p. 19.

M. Ali, et al., Book of Abstracts, VIII Int'l Conf. on Prostaglandins & Related Compounds, Montreal, Jul. 1992, abstract No. 54.

R. Apitz–Castro, et al., *Platelet Membrane I,* No. P1077.

R. Apitz–Castro, et al., *Platelet Pharmacology III,* No. 0747.

R. Aptiz–Castro, et al., Supplementary Abstracts, No. 2021 (1989).

S. Belman, et al., *Journal of Biochemical Toxicology,* 4, No. 3, 151–60 (1989).

K. Scharfenberg, et al., *Cancer Letters,* 53, 103–08 (1990).

A. Yoshida, et al., *Applied and Environmental Microbiology,* 53, No. 3, 615–17 (1987).

G. San–Blas, et al., *Antimicrobial Agents and Chemotherapy,* 33, No. 9, 1641–44 (1989).

U.P. Singh, et al., *Can. J. Bot.,* 68, No. 6, 1354–56 (1990).

Y. Gargouri, et al., *Biochemica et Biophysica Acta,* 1006, No. 1, 137–39 (1989).

S.F. Mohammad, et al., *Thrombosis Research,* 44, 793–806 (1986).

P.R. Mayeux, et al., *Prostaglandins 1,* 2936 at p. 660, vol. 45, No. 3 (1986) (abstract).

P.R. Mayeux, et al., *Agents and Actions,* 25, 182–90 (1988).

W. Tang, et al., *Chinese Drugs of Plant Origin: Chemistry, Pharacology, and Use in Traditional and Modern Medicine,* Chapter 11 (1988).

D. Mirelman, et al., *The Journal of Infectious Diseases,* 156, No. 1, 243–44 (1987).

A.K.A. Chowdhury, et al., *Indian Journal of Medical Research,* [A]93, 33–36 (1991).

D.R. Shalinsky, et al., *Prostaglandins,* 37, No. 1, 135–48 (1989).

M. Focke, et al., *FEBS Letters,* 261, No. 1, 106–08 (1990).

P.J. Kourounakis, et al., *Research Communication in Chemical Pathology and Pharmacology,* 74, No. 2, 249–52 (1991).

M. Liakopoulou–Kyriakides, et al., *Phytochemistry,* 24, No. 3, 600–01 (1985).

M. Liakopoulou–Kyriakides, *Phytochemistry,* 24, No. 7, 1593–94 (1985).

K. Nagai, *Japanese Journal of Infectious Diseases,* 47, 321–25 (1973).

A. Bordia, *Atherosclerosis,* 30, 355–60 (1978).

V. Esanu, *Rev. Roum, Med.–Virol.,* 32, No. 1, 57–77 (1981).

Y. Tsai, et al., *Chemical Abstracts,* 104, 24, No. 61572a (1986).

T. Bayer, et al., *Planta Medica,* 54, No. 6, 560, K1–6 (1988).

E. Block, *Scientific American,* 252, No. 3, 94–99 (1985).

J. Auger, et al., *Chemosphere,* 21, No. 7, 837–43 (1990).

H. Jansen, et al., *Planta Medica,* 53, No. 6, 559–62 (1987).

T.–H. Yu, et al., *Journal of Food Science,* 54, No. 4, 977–81 (1989).

K. Saito, et al., *Journal of the Association of Analytical Chemists,* 72, No. 6, 917–20 (1989).

S.J. Ziegler, et al., *Pharmaceutisch Weekblad Scientific Edition,* 9, No. 4, 248 (1987) (abstract).
E. Mochizuki, et al., *Journal of Chromatography,* 455, 271–77 (1988).
J.E. Lancaster, et al., *Phytochemistry,* 28, No. 2, 455–60 (1989).
J.E. Lancaster, et al., *Phytochemistry,* 28, No. 2, 461–64 (1989).
S.J. Ziegler, et al., *Journal of Liquid Chromatography,* 12, Nos. 1 & 2, 199–200 (1989).
S.J. Ziegler, et al., *Planta Medica,* 55, No. 4, 372–78 (1989).
L.P. Nock, et al., *Archives of Biochemistry and Biophysics,* 249, No. 1, 27–33 (1986).
L.P. Nock, et al., *Plant Physiology,* 85, No. 4, 1079–83 (1987).
K. Knobloch, et al., *Pharmaceutisch Weekblad Scientific Edition,* 9, 218 (1987).
K. Knobloch, et al., *Planta Medica,* 54, No. 6, K1–9, 561–62 (1988).
H. Jansen, et al., *Planta Medica,* 55, 434–49 (1989).
H. Jansen, et al., *Planta Medica,* 55, 440–45 (1989).
L.P. Nock, et al., *Phytochemistry,* 28, No. 3, 729–31 (1989).
T. Won, et al., *Physiologia Plantarum,* 77, No. 1, 87–92 (1989).
M. Fugita, et al., *Arch. of Biol. & Chem.,* 54, No. 4, 1077–79 (1990).
A. Rabinkov, et al., *Mechamisms of Action III,* 5, No. 4509, 1149 (1991) (abstract).
R. Gmelin, et al., *Phytochemistry,* 15, No. 11, 1717–21 (1976).
B. Iberl, et al., *Planta Medica,* 56, No. 2, 202–11 (1990).
B. Iberl, et al., *Planta Medica,* 56, No. 3, 320–26 (1990).
L.D. Lawson, et al., *Planta Medica,* 57, No. 3, 263–70 (1991).
S. Sendl, et al., *Planta Medica,* 57, No. 4, 361–62 (1991).
L.D. Lawson, et al., *Planta Medica,* 57, No. 4, 363–70 (1991).
G. Blania, et al., *Planta Medica,* 57, No. 4, 371–75 (1991).
T.–H. Yu, et al., *Journal of Agric. Food Chem.,* 37, No. 3, 725–30 (1989).
T.–H. Yu, et al., *Journal of Agric. Food Chem.,* 37, No. 3, 730–34 (1989).
T.–H. Yu, et al., *Journal of Food Science,* 54, No. 3, 632–35 (1989).
T.–H. Yu, et al., *Journal of Chromatography,* 462, 137–45 (1989).
L.D. Lawson, et al, *Journal of Natural Products,* 54, No. 2, 436–44 (1991).
Phillips et al., *Blood,* 71, 831–43 (1988).
Crowe, et al., *Workshop on Mechanisms and Specificity of HIV Entry into Host Cells,* pp. 57–70 (Düzgünes, ed. 1991).
Golding et al., *AIDS Res. Human Retrovir.,* 8, 1593–98 (1992).
Golding et al., *Aids Res. Human Retrovir.,* 8, 918 (1992).
Gruber et al., *AIDS Res. Human Retrovir.,* 7, 45–53 (1991).
Hansen et al., *Scand. J. Infect. Dis.,* 23, 31–36 (1991).
Hermanowski–Vosatka et al., *Cell,* 68 341–52 (1992).
Hildreth et al., *Science,* 244, 1075–1078 (1989).
Pantaleo et al., *Eur. J. Immunol.,* 21, 1771–74 (1991).
Pantaleo et al., *J. Exp. Med.,* 173, 511–514 (1991).
Patarroyo et al., *Immunol. Rev.,* 67–108 (1990).
Valentin et al., *J. Immunol.,* 144, 934–937 (1990).
Bachelot et al., *Biochem J.,* 284, 923–28 (1992).
Lawson et al., *Thrombosis Research,* 65, 141–56 (1992).

Oelkers et al., *Arzneim.—Forsch/Drug Res.,* 42, 136–39 (1992).
Sendl et al., *Atherosclerosis,* 94, 79–95 (1992).
Sendl et al., *Planta Med.,* 58, 1–7 (1992).
Siegel et al., *Z. Kardiologie 80 Supp. 7,* 9–24 (1991).
Singh et al., *Mycologia,* 84, 105–108 (1992).
Tadi et al., *Anticancer Research,* 11, 2037–2042 (1991).
Barillari et al., *Proc. Natl. Acad. Sci. USA,* 90, 7941 (1993).
Blood et al., *Biochim. Biophys. Acta,* 1032, 89–118 (1990).
Brake et al., *J. Cell Biol.,* Ill, 1275 (1990).
Cheresh et al., *J. Biol. Chem.,* 262, 17703–17711 (1987).
Crowe et al., in *Mechanisms and Specificity of HIV Entry into Host Cells,* 57–70 (Duzgunes ed., 1991).
Diegel et al., *AIDS Res. Human Retrovir.,* 9, 465 (1993).
Fecondo et al., *AIDS Res. Human Retrovir.,* 9, 733 (1993).
Fujita et al., *Jpn. J. Cancer Res.,* 83, 1317–26 (1992).
Golding et al., *AIDS Res. Human Retrovir.,* 8, 1593 (1992).
Gruber et al., *AIDS Res. Human Retrovir.,* 7, 45 (1991).
*Guidebook To The Extracellular Matrix And Adhesion Proteins,* p. 143 (Kreis et al. eds., 1993).
Guo et al., *J. Immunol.,* 151, 2225 (1993).
Hansen et al., *Scan J. Infect. Dis.,* 23, 31 (1991).
Hart et al., *Cancer and Metastasis Rev.,* 10, 115–128 (1991).
Hildreth et al., *Science,* 244, 1075 (1989).
Honn et al., *Exp. Cell Res.,* 201, 23–32 (1992).
Humphries et al., *Science,* 233, 467–70 (1986).
Hynes, *Cell,* 69, 11 (1992).
Johnson et al., *Proc. Natl. Acad. Sci. USA,* 86, 641 (1989).
Kalter et al., *Immunol. Letters,* 30, 219 (1991).
Kawaguchi et al., *Jpn. J. Cancer Res.,* 83, 1304–1316 (1992).
Knudsen et al., *J. Cell. Physiol.,* 136, 471–78 (1988).
Kramer et al., *Cancer Res.,* 49, 393–402 (1989).
Kramer et al., *Cancer and Metastasis Rev.,* 10, 49–59 (1991).
Meerloo et al., *J. Gen. Virol.,* 74, 129 (1993).
Mortarini et al., *Cancer Res.,* 52, 4499–4506 (1992).
Murata et al., *Jpn. J. Cancer Res.,* 83, 1327–1333 (1992).
Nip et al., *J. Clin. Invest.,* 90, 1406–1413 (1992).
Orentas et al., *AIDS Res. Human Retrovir.,* 9, 1157 (1993).
Pearce–Pratt et al., *Biology of Reproduction,* 48, 431 (1993).
Roossien et al., *J. Cell Biol.,* 108, 1979–83 (1989).
Saiki et al., *Jpn. J. Cancer Res.,* 81, 660–67 (1990).
Saiki et al., *Jpn. J. Cancer Res.,* 81, 668–75 (1990).
Saiki et al., *Jpn. J. Cancer Res.,* 81, 1003–1011 (1990).
Smole et al., *FASEB J.,* 6, A1714 (1992).
Soszke et al., *Exp. Cell Res.,* 196, 6–12 (1991).
Springer, *Nature,* 346, 425 (1990).
Thieblemont et al., *Clin. Exp. Immunol.,* 92, 106 (1993).
Ugen et al., *J. Natl. Cancer Inst.,* 80, 1461 (1988).
Valentin et al., *J. Immunol.,* 144, 934 (1990).
Van Muijen et al., *Int. J. Cancer,* 48, 85–91 (1991).
Vermot–Desroches et al., *Molec. Immunol.,* 28, 1095 (1991).
Vink et al., *Lab Invest.,* 68, 192–203 (1993).
Vogel et al., *J. Cell Biol.,* 121, 461 (1993).
Acosta et al., *Am. J. Hosp. Pharm,* 51, 2251–2267 (1994).
Allen et al., *Medical Hypothesis,* 45, 164–168 (1995).
Altieri et al., *Leukocyte Fibrinogen Receptor,* pp. 1893–1900, (1988).
Arthur et al., *Science,* 258, 1935–1938 (1992).
Asselot–Chapel, et al., HIV1 Infection Of Macrophages Results In Modulation of Fibronectin And $\alpha 5\beta 1$ Integrin Biosynthesis, IX International Conference On AIDS, PO–A12, p. 169 (1993).

Birdsall et al., *Journal of Leukocyte Biology*, 56, 310–317 (1994).
Blobel et al., *Nature*, 356, 248–252 (1992).
Bourinbaiar et al., *Acta. Virol.*, 37, 21–28 (1993).
Bourinbaiar et al., *Cellular Immunology*, 155, 230–236 (1994).
Bridges et al., *Antiviral Research*, 25, 169–175 (1994).
Butera et al., *Aids Research And Human Retorviruses*, 8, No. 6, 991–995 (1992).
Butini et al., ICAM–1/2/3 Molecules Function As Counter––Receptors For LFA–1 In HIV–Mediated Syncytia Formation, *IX International Conference On AIDS*, PO–A14, p. 182 (1993).
Butini et al., *Eur. J. Imunol.*, 24, 2191–2195 (1994).
Carlos et al., *Immunological Reviews*, 114, 5–28 (1990).
Chehimi et al., *Journal Of General Virology*, 74, 1277–1285 (1993).
Clapham et al., *Phil. Trans. R. Soc. Lond. B*, 342, 67–73 (1993).
Coller et al., *Circulation*, 80, No. 6, 1766–1774 (1989).
Collman et al., *Seminars In Virology*, 3, 185–202 (1992).
Connor et al., *The New England Journal Of Medicine*, 331, No. 18, 1173–1180 (1994).
Cook et al., *Thrombosis and Haemostasis*, 70, No. 5, 838–847 (1993).
Denis, *the Journal Of Immunology*, 153, 2072–2081 (1994).
Douglas et al., *Journal Of Reproductive Immunology*, 24, 49–62 (1994).
Dullege et al., *VIII International Conference On AIDS*, "Transplacental Transfer Of ICD4–IgC Given One Week And Immediately Prior To Birth: Safety And Pharmacokinetics In HIV–1 Seropositive Pregnant Woment And Their New Born Infants," PoB 3028 (1992).
Falanga et al., *Eur. J. Immunol.*, 21, 2259–2263 (1991).
Faurc et al., *Virus Research*, 34, 1–13 (1994).
Ferguson et al., *Proc. Natl. Acad. Sci. USA*, 88, 8072–8076 (1991).
Fletcher et al., *Journal Of Clinical Pharmacy And Therapeutics*, 18, 375–388 (1993).
Gehlsen et al., *Clin. Exp. Metastasis*, 10, 111–120 (1992).
Glander et al., *International Journal Of Andrology*, 16, 105–111 (1993).
Gonzalez–Scarano et al., *Seminars In Virology*, 3, 225–234 (1992).
Gougeon et al., *Science*, 260, 1269–1270 (1993).
Grau et al., *Eur. J. Immunol.*, 21, 2265–2267 (1991).
Guo et al, *Aids Research And Human Retroviruses*, 11, 1007–1013 (1995).
Hamilton et al., *The New England Journal Of Medicine*, 326, 437–443 (1992).
Hardan et al., *Int. J. Cancer*, 55, 1023–1028 (1993).
Harning et al., *Clin. Exp. Metastasis*, 11, 337–342 (1993).
Haynes, *Science*, 260, 1279–1286 (1993).
Huitinga et al., *Eur. J. Immunol.*, 23, 709–715 (1993).
Isberg et al., *Trends In Microbiology*, 2, No. 1, 10–14 (1994).
Ishizuka et al., *Int. J. Immunopharmacol.*, 17, No. 2, 133–139 (1993).
Ito et al., *Journal Of Virology*, 66, No. 17, 5999–6007 (1992).
Johnson, "New Developments In Antiretroviral Drug Therapy for HIV Infection," *AIDS Clinical Review*, pp. 70–104 (1992).
Johnston, *Science*, 260, 1286–1293 (1993).
Kavanaugh et al., *Arthritis & Rheumatism*, 37, 992–999 (1994).
Kazazi et al., *Journal Of General Virology*, 75, 2795–2802 (1994).
Kolson et al., *AIDS Research And Human Retroviruses*, 9, No. 7, 677–685 (1993).
Larson et al., *Immunological Reviews*, 114, 181–216 (1990).
Levy, *Mechanisms And Specificity Of HIV Entry Into Host Cells*, Adv. Exp. Med. Biol., 300, pp. 1–15 (1991).
Li et al., *Science*, 268, 429–431 (1995).
Locher et al., *Clin. Exp. Immunol.*, 98, 115–122 (1994).
Mitsuya et al., *The FASEB Journal*, 5, 2369–2381 (1991).
*MMWR (Morbidity And Mortality Weekly Report)*, 43, No. 16, 285–287 (Apr. 29, 1994).
Mohan, *Drug Development Research*, 29, 1–17 (1993).
Mould et al., *The Journal of Biological Chemistry*, 266, No. 6, 3579–3585 (1991).
Mousa et al., *Circulation*, 89, No. 1, 3–12 (1994).
Nemerow et al., *Trends In Cell Biology*, 4, 52–55 (1994).
Ohta et al., *The EMBO Journal*, 13, No. 9, 2004–2055 (1994).
Palmer et al., *Clin. Exp. Immunol.*, 93, 344–349 (1993).
Pantaleo et al., *Current Opinion In Immunology*, 6, 600–604 (1994).
Paul, *Science*, 267, 633–636 (1995).
Perez, *Antimicrobial Agents And Chemotherapy*, 38, No. 2, 337–339 (1994).
Phillips, *AIDS*, 8, 719–731 (1994).
Reinhardt et al., "Neurocognitive Disorder Is Associated With With High–Replicating, Syncytia Inducing HIV–1 Isolates In Cere–brospinal Fluid," *IX International Conference On AIDS*, PO–A14–0285, p. 182 (1993).
Reynolds–Kohler et al., *Mechanisms And Specificity Of HIV Entry Into Host Cells*, pp. 27–44 (1991).
Rossen et al., *Trans. Ass. Am. Pysicians*, 102, 117–130 (1989).
Sato et al., *Virology*, 186, 712–724 (1992).
Scarborough et al., *The Journal Of Biological Chemistry*, 268, No. 2, 1058–1065 (1993).
Schuitemaker et al., *Journal Of Virology*, 66, No. 3, 1354–1360 (1992).
J.C., "What Causes The Immune System Collapse Seen In Aids?", *Science*, 260, 1256 (1993).
Shebuski et al., *Thrombosis And Haemostasis*, 64, No. 4, 576–581 (1990).
Sheu et al., *J. Lab. Clin. Med.*, 123, No. 2, 256–263 (1994).
Stent et al., *Journal Of Leukocyte Biology*, 56, 304–309 (1994).
Stevenson et al., *AIDS Research And Human Retroviruses*, 8, No. 2, 107–117 (1992).
Tabata et al., *The Journal Of Immunology*, 153, 3256–3266 (1994).
Taichman et al., *Cell Regulation*, 2, 347–355 (1991).
Tang et al., *Int. J. Cancer*, 54, 338–347 (1993).
Tcheng et al., *Circulation*, 90, No. 4, 1757–1764 (1994).
Trikha et al., *Cancer Research*, 54, 4993–4998 (1994).
Weeks et al., *The Journal Of Cell Biology*, 114, 847–853 (1991).
Aboulker et al., *The Lancet*, 341, 889–890 (Apr. 3, 1993).
Yarchoan et al., *J. Enzyme Inhibition*, 6, 99–111 (1992).
Yarchoan et al., *Blood*, 78, No. 4, 859–884 (1991).
Zahalka et al., *The Journal Of Immunology*, 150, 4446–4477 (1993).
Harlan, 1991, *Schweiz. Med. Wschr.*, 121:7.
Ikeda et al., 1995, *Infect. Immun.*, 63:4812.
Issekutz et al., 1995, *J. Exp. Med.*, 181:1197–1203.
Issekutz et al., 1996, *J. Exp. Med.*, 183:2175–2184.

Mazzone et al., 1995, *Haematologica,* 80:161.
Talbott et al., 1994, *New Horizons,* 2:545.
Vedder et al., 1988, *J. Clin. Invest.,,* 81:939.
Vedder et al., 1989, *Surgery,* 106:509.
Delaha et al., 1985, *Antibmicrob. Agents Chemother.,* 27(4):485–6.
Demers et al., *Chem. Abstracts,* 116:128198 (1992).
Douvas et al., 1991, *Proc. Natl'l Acad. Sci USA,* 6328–6332.
Meng et al., 1990, *Nutr. Cancer,* 14(3–4):207–17.
Merck Index, No. 185 (1989).
Mohr, 1987, *Gordian,* 87(10):195–6 and English translation.
Nakagawa et al., 1989, *Chem. Abstracts,* 111:146760e.
Nakagawa et al., 1989, *Phytotherapy Res.,* 3:50–53.
Nakata, 1973, *Nippon Eiseigaku Zasshi,* 27(6):538–43 and English translation.
Nishikawa et al., *Chem. Abstracts,* 74:30034j (1971).
Qian et al., 1986, *Contraception,* 34(3):295–302.
Sabata et al., *Chem. Abstracts,* 508135 (1986).
Shah et al., 1990, *Fitoterapia,* 61(2):121–6.
Sumiyoshi et al., 1990, *Cancer Res.,* 50(16):5084–7.
Tsai et al., 1985, *Planta Medica,* pp. 460–461.
Hemler, in Guidebook to the Extracellular Matrix, pp. 143–145 (Kreis and Vale eds. 1993).
Holmes et al., 1994, *AIDS Res. Hum. Retrovir.,* 10:S53.
Pigott and Power, The Adhesion Molecule Facts Book, pp. 9–12.

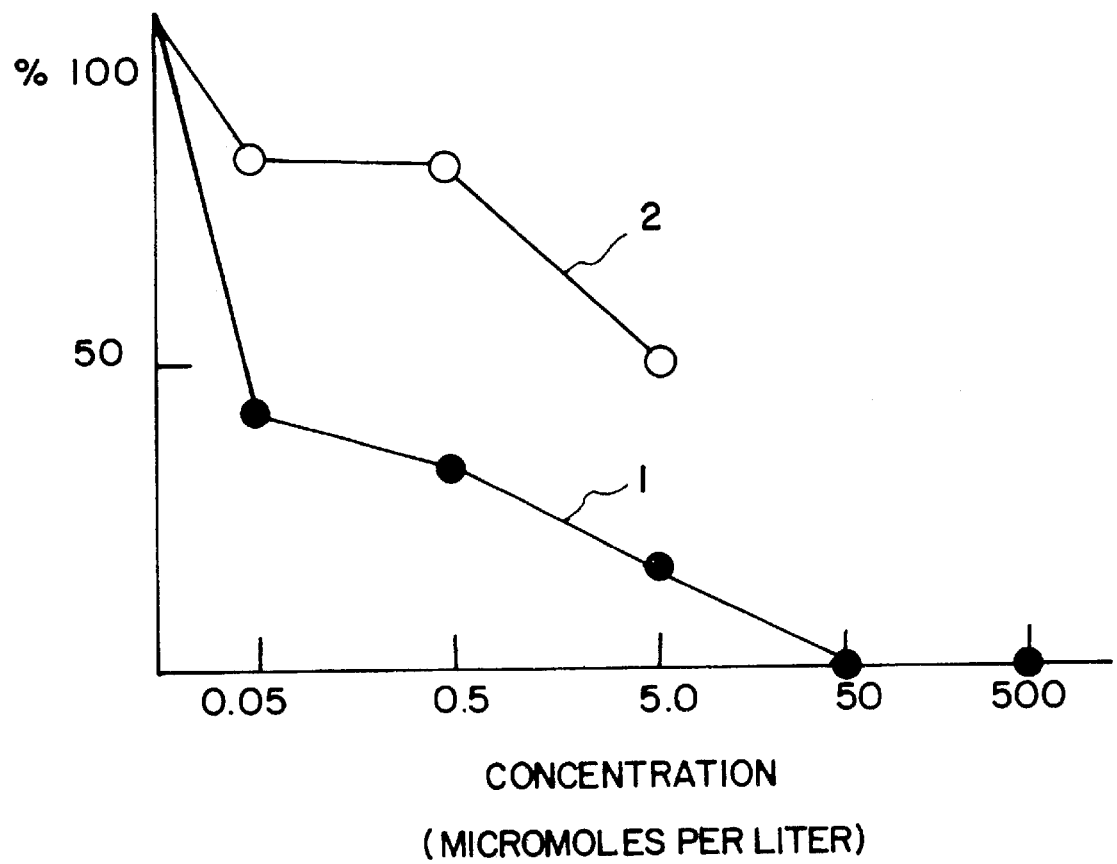

METHODS OF USING AJOENE

This application is a continuation-in-part of pending application Ser. No. 08/445,146, filed May 19, 1995, which was a continuation-in-part of application Ser. No. 07/906, 850, filed Jun. 30, 1992, now abandoned.

BACKGROUND OF THE INVENTION

Ajoene is 4,5,9-trithiadodeca-1,6,11-triene-9-oxide, having a structural formula as follows:

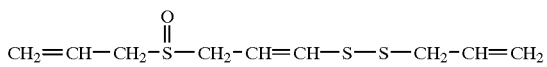

Ajoene, and a precursor thereof, can be isolated from extracts of garlic (*Allium sativum*). As the garlic is crushed, alliin in the garlic comes into contact with allinase in the cell wall to form allicin. Then, in the presence of a polar molecule such as a lower alcohol or even water, allicin forms Ajoene.

Ajoene has been previously shown to inhibit platelet aggregation by inactivating allosterically the platelet integrin, GP IIb/IIIa (Apitz-Castro R. et al.: *Biophys. Res. Commun.*, 1986, 141:145). This inhibition of integrins by Ajoene is reversible.

Also, integrin-mediated formation of cell-to-cell contacts has been shown to typically be a prerequisite for membrane fusion (Hildreth, J. E. K. and Orentas, R. J., Science, 1989, 244:1075).

DESCRIPTION OF THE INVENTION

By this invention, safe and effective doses of Ajoene may inhibit the progression of an HIV infection in a patient. Specifically, stereoisomer mixtures of Ajoene may be used, although pure (E) and (Z) stereoisomer forms may also be used.

One of the characteristics of an HIV infection so inhibited is the formation of HIV-induced syncytia, in which HIV target cells such as lymphocytes and monocytes fuse together to form giant, multinucleate cells in HIV-infected patients. This inhibiting effect would require a sufficient dose to provide a concentration of Ajoene of at least 50 nanomoles per liter of blood plasma in the patient, and preferably at least 200 nanomoles of Ajoene per liter of plasma. Transfer of genetic material between cells will, therefore, also be inhibited by Ajoene.

Additionally, it appears that Ajoene inhibits the growth of HIV-infected cells, HIV, and other viruses, also inhibits the incorporation of HIV into CD4-negative cells. For this purpose, Ajoene is preferably administered in sufficient dose to provide a concentration of at least 5,000 nanomoles per liter of patient's blood plasma, although lesser concentrations may also be effective.

In addition to infections caused by HIV and other viruses of the Retroviridae family, Ajoene can be used to treat infections caused by Herpesviridae (e.g., herpes simplex, varicella zoster, Epstein-Barr virus, and cytomegaly virus), Hepadnaviridae (e.g., hepatitis B), Picornaviridae (e.g., hepatitis A virus and poliomyelitis virus), Orthomyxoviridae (e.g., influenza virus), Poxviridae (e.g., variola virus and vaccinia virus), Flaviviridae (e.g., yellow fever virus and hepatitis C virus), Rubiviridae (e.g., rubella virus), Paramyxoviridae (e.g., measles, parainfluenza, mumps and canine distemper viruses), Rhabdoviridae (e.g., rabies virus), Papovaviridae (e.g., papillomavirus) and Adenoviridae.

Additionally, the growth of tumors such as T-lymphomas and the development of melanoma metastasis may be inhibited by administering to the patient, human or animal, a safe and effective dosage of Ajoene, preferably to provide a concentration of Ajoene to the patient of at least 50 micromoles per liter of the patient's blood plasma, or at least in the blood adjacent the tumor, for example in cases of regional perfusion where steps are taken to minimize the concentration of Ajoene elsewhere in the body except at the tumor site.

Ajoene serves as an agent that inhibits the aggregation of blood cells, such as platelets and neutrophils. Ajoene may, therefore, exhibit benefit as an agent for the treatment of pathologies derived from aggregation of these cells, including, in part, the effects of shock. In cases of shock, platelets and neutrophils aggregate in the blood vessels of the lungs, which may be a primary cause of death in that oxygen transfer through the lungs is degraded, leading to death. Ajoene may thus counteract at least part of the effects of shock, for example in sepsis, anaphylaxis, or in blood loss. The inhibiting effect of Ajoene in this use would typically be the result of a dose to provide a concentration of Ajoene of at least 10 micromoles per liter of the patient's blood plasma.

Ajoene can also be administered in effective dosage to suppress many inflammation processes, for example, those inflammation processes that occur in the lungs as a consequence of severe shock. Inflammation is a typical pathological process (i.e., either inherent in or associated with a variety of distinct diseases and illnesses), defensive in nature, but potentially dangerous if uncontrolled. There are several indices of inflammation at the "whole body" level: e.g., hemodynamic disorders (e.g., hyperemia and edema), pain, temperature increment, and functional lesion. At the cellular level, inflammation is characterized by leukocyte emigration into tissues (where they phagocytose bacteria, viruses, or other invaders) and platelet aggregation (to localize the infection), which emigration and aggregation may also have a destructive effect on tissue. At the molecular level, inflammation is characterized by activation of at least three plasma defense systems (complement, kinin, and coagulation cascades), and by synthesis of cytokines and eicosanoids. When inflammation is generalized, as in the case of shock, the various indices of inflammation may become disseminated and occur throughout the entire organism.

Without wishing to be limited to any particular mechanism of operation of Ajoene, it is believed that the beneficial effects of Ajoene are achieved because Ajoene is an inactivating agent for several integrin receptors of cells. Thus, it is believed that other inactivating agents for cell integrin receptors may exhibit similar benefits as Ajoene, particularly with respect to the suppression of adhesion events mediating HIV spread in the body (e.g., adhesion-induced HIV budding, infection of CD4- cells, cell-to-cell transmission of infection by cell fusion, infection by virus having adhesion molecules captured from host cells, syncytia formation in the central nervous system). Preferred are non-antibody inactivating agents for integrins. Particularly preferred are small (low molecular weight), non-antibody inactivating agents which are not peptides corresponding to the binding portion of the normal protein ligands for integrins.

As a result of its ability to inactivate integrins, Ajoene can be used to treat any disease caused by, or involving, integrin-mediated functions. For instance, Ajoene can be used to inhibit virus-cell fusion or undesired cell-cell fusion. Undesired cell-cell fusion can include cell-cell fusion (transitory or permanent) that results in the transfer of viral genetic material.

Work by others has shown that HIV-1 Tat protein stimulates the growth of AIDS-Kaposi's sarcoma (AIDS-KS) cells by interacting with the integrins $\alpha_5\beta_1$ and $\alpha_v\beta_3$. Ajoene should, therefore, be effective in treating Kaposi's sarcoma in view of its ability to inactivate integrins.

The above disclosure and the examples below are for illustrative purposes only, and are not intended to limit the invention of this application, which is as defined in the claims below.

EXAMPLE 1

Ajoene as an Inhibitor of HIV-Mediated Syncytia Formation

Intact H9 cells and chronically infected H9:RF cells (a cloned population of H9 cells harboring HIV genome) were maintained in suspension in RPMI-1640 medium supplemented with 10% (v/v) heat-inactivated fetal calf serum, 50 micrograms/ml gentamycin and 2 mM L-glutamine. Syncytium formation was assessed by co-cultivation of H9 cells and H9:RF cells (2:1) for 16 hrs with various concentrations of Ajoene in 96-well flat-bottomed plates, $3\times10^5$ cells per well. By the end of the incubation period syncytia were counted. $IC_{50}$ for Ajoene was calculated by plotting relative amount of syncytia (percent of the syncytia formed in the absence of the compound) against Ajoene concentration. If not specified otherwise, Ajoene was used as a 1:1 mixture of (E)- and (Z)-stereoisomers.

Specifically, Ajoene inhibited fusion of intact H9 cells with HIV-infected H9:RF cells ($IC_{50}$ of 50 nanomoles per liter Ajoene concentration at 16 hrs incubation).

EXAMPLE 2

Ajoene as an Inactivator of Several Distinct Integrin Receptors

Platelet aggregation was measured turbidimetrically on a standard platelet aggregometer equipped with a recorder. Samples of platelet-rich plasma (PRP) were standardized with respect to the cell density ($3\times10^8$ per ml); maximal light transmission (LT) was calibrated with platelet-poor plasma (PPP). Aliquots of PRP (0.25 ml in glass cuvettes) were stirred in the cell of the device (1000 rpm, 37° C.) with Ajoene (0–100 micromoles per liter final concentration) for 1 min., followed by addition of the stimuli. LT increments were traced for 5 min. Maximal rate of aggregation was derived from the slope of each curve; $IC_{50}$ for Ajoene was determined by a method such as that described in Vrzheshch P V, Tatarintsev A V, Yershov D E et al.: Cell Response Kinetics: the Phenomenon of Supercooperativity in Aggregation of Human Platelets. *Dokl. Akad. Nauk SSSR*, 1989, 307:477 (in Russian). Neutrophil aggregation was assayed as described above for the platelet system, with some modifications. Freshly isolated neutrophils were finally suspended in a buffer (120 mM NaCl, 4 mM KCl, 10 mM dextrose, 2 mM $CaCl_2.2H_2O$, 2 mM $MgCl_2.6H_2O$, and 20 mM Tris; pH 7.4) to the final density of $10^7$ cells per ml. Aliquots of neutrophil suspension (0.25 ml in siliconized glass cuvettes; $10^7$ cells per ml) were stirred in the cell of the aggregometer with 5 micrograms per ml cytochalasin·B (1000 rpm, 37° C.) for 1 min. Ajoene (0–50 micromoles per liter) and N-formyl-L-methionyl-L-leucyl-L-phenylalanine ($10^{-7}$ M) were then introduced into the suspension sequentially, with an interval of 1 min. Maximum LT (100%) was calibrated with the same buffer. H9 and Jurkat cells were cultured as described above in Example 1.

Ajoene inhibited platelet aggregation in PRP with an $IC_{50}$ of about 50 micromoles per liter. Ajoene blocked N-formyl-L-methionyl-L-leucyl-L-phenylalanine-stimulated neutrophil aggregation ($IC_{100}$ of about 10 micromoles per liter) and caused rapid deaggregation when added to aggregated neutrophils. The clusters normally formed by H9 and Jurkat cells in culture were disrupted by Ajoene with an $IC_{50}$ of about 50 nanomoles per liter.

Though the requirement of integrins for contact interactions in either of these systems has long been established, the molecular mechanisms are clearly nonidentical. It is known that in platelets the relevant integrin is GP IIb/IIIa. Neutrophils form contacts via interaction of LFA-1 and/or Mac-1 with their surface counterstructures, while cohesion of T-cells is supported by LFA-1 and by fibronectin-binding VLA integrins. Hence, Ajoene is apparently capable of inactivating integrin receptors of at least three distinct subfamilies ($\beta_1$, $\beta_2$ and $\beta_3$). One probable mechanism is that the compound either binds to a region which is highly conserved within the members of the integrin superfamily, or somehow alters the microenvironment, thereby inactivating the whole receptor. At the cellular level this inactivation appears as a severe (but controllable) deficiency in the respective cell-specific integrins, i.e., inability for aggregation (platelets, neutrophils), disintegration of cell clusters (intact H9 and Jurkat cells), failure to fuse (HIV-infected cells; Example 1).

EXAMPLE 3

Ajoene as an Inhibitor of HIV Replication

LAV-BRU 1 isolate of HIV-1 and RF isolate of HIV-1 were propagated in CEM and H9 cells, respectively. A 20-ml log-phase culture containing $7\times10^5$ cells per ml was incubated at 37° C. for 24 hrs. Cultures with less than 10% trypan blue stained cells were used as a source of virus. To harvest HIV particles, producer cells were pelleted by centrifugation (400 g, 5 min) and the supernatant containing HIV-1 particles was filtered through a 0.45 micrometer Millipore filter, aliquoted and stored at –80° C. The titer of HIV-1 ranged from $1\times10^5$ to $2\times10^5$ $CCID_{50}$ (50% cell culture infective dose). To determine whether Ajoene could also influence HIV replication, CEM13 and H9 cells were inoculated with appropriate amounts of HIV (LAV-BRU 1 and RF, respectively), to give an m.o.i. (multeity of infection) of 0.1 in either experimental setting. Ajoene (or its vehicle) was added to $10^7$ infected cells resuspended in the growth medium and the cells were plated in 96-well flat-bottomed plates. After 72 hrs the bulk of HIV antigens was measured by solid phase immunoassay as described in Zhdanov V M, Karamov E V, Arakelov S A, et al.: An Enzyme Immunoassay for Detection of Antigen and Antibody to Human Immunodeficiency Virus and the Use Thereof For serological Survey of Different Population Groups. *Vop Virusol* 1988, N3:292 (in Russian). In a series of separate experiments Ajoene was introduced into plated cell cultures stepwise, i.e. in aliquots of 50 nanomoles per liter concentration per 12 hrs of incubation, the first addition coinciding with the moment of inoculation.

Replication of HIV-1 (RF) in H9 cells was inhibited with an $IC_{50}$ of 25 micromoles per liter (m.o.i. 0.1; 72 hrs of incubation). Assessment of HIV-1 (LAV-BRU 1) replication in CEM13 cells under the same experimental conditions revealed a more pronounced anti-viral activity ($IC_{50}$ of about 5 micromoles per liter concentration). A considerable increase in the latter became evident when the concentration of the compound was increased stepwise (50 nanomoles per liter concentration per 12 hrs of incubation; CEM13—LAV-BRU 1 system; inhibition by 30%; total concentration 0.25 micromoles per liter; m.o.i. 0.1; 72 hrs of incubation).

EXAMPLE 4

Ajoene as a Potential Anti-Shock Agent

Neutrophil aggregation within the lung microvasculature is known to be a key event in the development of the so-called adult respiratory distress syndrome (ARDS), the main cause of death in patients suffering shock. Also, administration of neutrophil-aggregating agents (such as phorbol-myristate-acetate, complement anaphylotoxins or N-formyl-L-methionyl-L-phenylalanine, calcium ionophore A23187, arachidonic acid, platelet-activating factor) to laboratory animals results in the development of ARDS. Some inhibitors of neutrophil aggregation, such as antagonists of the platelet-activating factor, have been shown to prevent lethality in experimental septic shock, Toyofoku T. et al.: Effects of ONO-6340, a Platelet-Activating Factor Antagonist, on Endotoxin Shock in Unanesthetized Sheep. Prostaglandins, 1986, 31:271). It is believed that beneficial effects of glucocorticoids in various shock states are largely due to their ability for inhibition of neutrophil aggregation (Hammerschmidt, et al., J. Clin. Invest. 1979, 63:798; Cronstein, B. N. et al., Proc. Natl. Acad. Sci. USA, 1992, 89: 9991–99).

The antiaggregatory activity of Ajoene disclosed in Example 2 above is sufficiently high to expect that Ajoene will be effective both for the prevention and treatment of various shock states by suppressing such aggregation.

EXAMPLE 5

Ajoene as an Antineoplastic Agent

Leukemic (CEM, MT2, MT4) and lymphoid (H9, Jurkat) T-cells were cultured as described above (Example 1) with various concentrations of Ajoene, and the toxic effects were assessed by the cytocidal activity ($LD_{100}$).

For T-lymphoid tumor cells, $LD_{100}$ was achieved after 72 hrs of culturing in a media of about 50 micromoles of Ajoene per liter.

For Leukemia T cells $LD_{100}$ was achieved after 72 hrs of culturing in a media of about 500 micromoles of Ajoene per liter.

EXAMPLE 6

Ajoene as an Antimetastatic Agent

Male C57BL/6 mice were used as experimental animals. Murine platelet aggregation was measured as described above (Example 3). To evaluate the effect of the compound on experimental metastasis, a suspension of $10^5$ melanoma B16 cells was pretreated for 30 min with Ajoene or its vehicle, and the suspension (including Ajoene or its vehicle) was injected intravenously into mice. The mice were sacrificed 3 weeks post-injection, and their lungs subjected to microscopic examination. To evaluate the effect on tumor cell implantation, mice were inoculated subcutaneously with $10^6$ B16 cells (pretreated for 15 min with Ajoene or its vehicle) in their pretreatment medium, and the volume of the tumors formed was measured 14 and 21 days after the injection.

Ajoene inhibited ADP-induced aggregation of PRP with an $IC_{100}$ of 200 micromoles per liter. Pretreatment of B16 cells with Ajoene (200 micromoles per liter) rendered them incapable of colonizing lungs. Subcutaneous implantation was prevented by exposing the cells to 2500 micromolar concentration of Ajoene. At 2.5 micromolar concentration of the compound, the volume of melanomas was reduced by one-half.

EXAMPLE 7

Integrin-Inactivating Properties of Ajoene are not Stereospecific

Synthetic stereoisomers of Ajoene exhibited equal antiaggregatory activity ($IC_{50}$ of about 50 micromolar concentration of Ajoene for platelets, $IC_{100}$ of about 10 micromolar concentration of Ajoene for neutrophils).

EXAMPLE 8

Ability of Ajoene to Protect Cells From Infection With Cell-Free Viruses

The effect of Ajoene in protecting against HIV infection was evaluated using polymerase chain reaction (PCR) analysis which recognized amplified DNA sequences of HIV gag gene. MT-4 cells were used as target cells and strain IIIB of HIV-1 was used as inoculate. Serial dilutions of Ajoene or an equivalent volume of its vehicle were added to MT-4 cells, followed by addition of a sufficient amount of free virus ($<10^3$ particles per cell). The protective effect of Ajoene was monitored by examining for the absence or presence of proviral HIV DNA in target cells 16 hours after the inoculation. Ajoene completely prevented HIV infection at the minimal dose of 4 µg/ml (17 micromoles per liter) and had an $IC_{50}$ of 5 micromoles per liter.

The effect on herpes simplex virus (HSV) infection was assessed using human embryonic lung fibroblast line WI-38 and HSV-2 strain G (derived from a human with the genital infection). Semiconfluent fibroblast monolayers grown in 96-well culture plates ($10^5$ cells per well) were exposed to serial dilutions of Ajoene or vehicle control, followed immediately by addition of HSV-2 (5000 $TCID_{50}$ per well). After 24 hours of culturing, the supernatants were examined by ELISA for the content of HSV antigens. Ajoene completely prevented HSV infection at 4 µg/ml (17 micromoles per liter) and had an $IC_{50}$ of 6 micromoles per liter.

Referring to FIG. 1, the effect of Ajoene on syncytia formation and HIV replication is shown.

For curve 1, the effect of Ajoene on the infusion of cultured, intact H9 cells with HIV infected H9:RF cells is disclosed. For this curve, the vertical graph axis pertains to the maximum amount of syncytia formed in the absence of Ajoene (100 percent), while the points on line 1 represent percentages of such an amount of syncytia formed in the presence of varying concentrations of Ajoene (micromoles per liter). The $IC_{50}$ of syncytia formation was found at a concentration of 0.045 micromole of Ajoene per liter. Essentially no syncytia were found at a concentration of 50 micromoles of Ajoene per liter.

Referring to curve 2, the antiviral activity of Ajoene is shown, as assessed by the inhibition of HIV-1 (Lav—BRU 1) replication in cultured CEM13 cells. Here, the vertical axis represents the percentage of HIV antigens detected by solid phase immunoassay (previously mentioned) in the absence of Ajoene.

The $IC_{50}$ was achieved under these conditions at about a 5 micromolar concentration of Ajoene.

Thus, Ajoene exhibits significant potential as an effective anti-HIV drug to reduce or eliminate the course of the disease while exhibiting relatively low toxic effects. Ajoene is also effective against other viruses, many tumor cells and tumor metastasis. In addition, Ajoene exhibits significant potential as an effective drug to block cell aggregation and fusion, for example in various shock states. Finally, Ajoene may be used to treat inflammation. In general, Ajoene may be used to treat any disease or condition caused by, or involving, integrin-mediated cellular functions.

To treat one of these conditions, an effective amount of Ajoene is administered. Effective dosage forms, modes of administration and dosage amounts, may be determined empirically, and making such determinations is within the skill of the art. It is understood by those skilled in the art that the dosage amount will vary with the intended use, the severity of a disease or other condition, the route of administration, the rate of excretion, the duration of the treatment, the identity of any other drugs being administered, the age, size and species of the animal, and like factors well known in the medical and veterinary arts. In general, a suitable daily dose of Ajoene will be that amount of the compound which is the lowest dose effective to produce a therapeutic effect. However, the total daily dosage will be determined by an attending physician or veterinarian within the scope of sound medical judgment. If desired, the effective daily dose of Ajoene may be administered as two, three, four, five, six or more sub-doses, administered separately at appropriate intervals throughout the day.

Ajoene may be administered in any desired and effective manner: as a pharmaceutical preparation for oral ingestion, or for parenteral or other administration in any appropriate manner such as intraperitoneal, subcutaneous, topical, inhalation, intrapulmonary, rectal, vaginal, sublingual, intramuscular, intravenous, intraarterial, intrathecal, or intralymphatic. For instance, the topical application of Ajoene to mucous membranes (in the form of creams, gels, suppositories and other known means of topical administration) can be used to prevent HIV infection of mucosal cells, an important route of HIV transmission. In addition, intralymphatic administration of Ajoene may be advantageous in preventing the spread of HIV within the body. Further, Ajoene may be administered in conjunction with other anti-viral drugs, other chemotherapy agents for tumor or metastasis treatment, and other anti-shock or anti-inflammation drugs or treatments. The Ajoene may be encapsulated or otherwise protected against gastric or other secretions, if desired. Ajoene is desirably incorporated into liposomes or time-release compositions for administration.

As noted above, other inactivating agents for cell integrin receptors may be used in place of Ajoene. These agents may be used in a manner similar to the manner in which Ajoene is used, and suitable doses may be determined as described above.

The above description has been offered for illustrative purposes only and is not intended to limit the scope of the invention of this application, which is as described in the claims below.

I claim:

1. A method of treating inflammation comprising administering to an animal suffering from inflammation an effective amount of an agent which is an integrin inhibitor.

2. The method of claim 1 wherein the agent is ajoene.

* * * * *